United States Patent [19]

Schinitsky

[11] Patent Number: 4,473,551
[45] Date of Patent: Sep. 25, 1984

[54] ANTI-INFLAMMATORY COMPOSITION

[75] Inventor: Michael Schinitsky, Madison, Wis.

[73] Assignee: Faxon Pharmaceuticals, Inc., Madison, Wis.

[21] Appl. No.: 502,716

[22] Filed: Jun. 9, 1983

Related U.S. Application Data

[63] Continuation-in-part of Ser. No. 410,447, Aug. 23, 1982, abandoned.

[51] Int. Cl.³ ............................................. A61K 35/32
[52] U.S. Cl. ...................................... 424/95; 424/180
[58] Field of Search .................................. 424/95, 180

[56] References Cited

U.S. PATENT DOCUMENTS 3,400,199 9/1968 Balassa .................................. 424/95
4,350,682 9/1982 Balassa .................................. 424/95

OTHER PUBLICATIONS

Rovati et al.—Chem. Abst., vol. 80 (1974), p. 74329n.
Lauscher—Chem. Abst., vol. 77 (1972), p. 130609f.
Blazkovek et al., *Int. Arch. Allergy*, 27, 289–303 (1965).
Crolle et al., *Current Medical Research and Opinion*, 7, 104–109 (1980).
D'Ambrosio et al., *Pharmatherapeutica*, 2, 504–508 (1981).
Houck et al., *Surgery*, 51, 632–638 (1962).
Lattes et al., *Am. J. Pathology*, 32, 979–991 (1956).
Prudden et al., *Archives of Surgery*, 86, 157–161 (1963).
Prudden, *Archives of Surgery*, 89, 1046–1059 (1964).
Prudden et al., *Am. J. Surgery*, 119, 560–564 (1970).

*Primary Examiner*—Sam Rosen
*Attorney, Agent, or Firm*—Barnes & Thornburg

[57] ABSTRACT

A composition and method for the treatment of disorders having an inflammatory component comprising essentially whole cartilage, or a greater than 100,000 molecular weight fraction obtained from an aqueous extract thereof, in combination with glucosamine or a substance affording glucosamine under the conditions of treatment, administered topically or parenterally.

21 Claims, No Drawings

ANTI-INFLAMMATORY COMPOSITION

This application is a continuation-in-part of my application Ser. No. 410,447, filed Aug. 23, 1982 abandoned.

The present invention relates to the treatment of disorders having an inflammatory component. More particularly, it relates to improved anti-inflammatory therapeutic compositions and to the use thereof in the treatment of the various forms of arthritis and related systemic conditions, as well as such topical disorders as psoriasis, acne, and the like.

Nearly a century ago, aspirin became available as a drug for use as an antipyretic and anti-inflammatory agent and has continued to be the most widely used drug for such purposes, despite the subsequent appearance of the corticosteroids, the propionic acid derivatives, the indole derivatives, the phenylacetic acid derivatives, the pyrazoles and derivatives, the fenamates, the substituted triaryls, the quinazolinones, gold salts, D-penicillamine, levamisole, and chloroquine. All of these drugs, including aspirin, have potentially serious side effects, and none are curative. A need therefore continues to exist for an improved therapeutic agent for use against the various inflammatory disorders.

The literature reports a number of studies on the therapeutic use of cartilage from various sources and in various forms. Houck et al, *Surgery*, 51, 632-638 (1962), used finely ground bovine cartilage to inhibit inflammation and to promote wound healing. Lattes et al, *American Journal of Pathology*, 32, 979-991 (1956), carried out similar tests on cortisone-treated animals. Prudden, *Archives of Surgery*, 89, 1046-1059 (1964), compared cartilage from various sources and found powdered shark cartilage to be superior in speeding wound repair.

Prudden et al, *Archives of Surgery*, 86, 157-161 (1963), carried out a water extraction on bovine trachea and tested the extract for wound healing. He found it to be inactive.

In searching for the active component of cartilage, Prudden et al, *American Journal of Surgery*, 119, 560-564 (1970), observed that glucosamine is capable of accelerating the wound-healing process. Furthermore, D'Ambrosia et al, *Pharmatherapeutica*, 2, 504-508 (1981), successfully used glucosamine in the treatment of osteoarthritis.

In my earlier application, referred to above, I reported my discovery that shark cartilage is greatly superior to cartilage from other sources in the treatment of inflammatory disorders, and I further reported that a combination of shark cartilage with glucosamine exhibits a strongly synergistic effect in the treatment of inflammatory disorders.

I have now further discovered that the synergistic effect of glucosamine in the treatment of inflammatory disorders extends broadly to cartilages from whatever source derived, including shark and other marine dwellers, cattle, hogs, chicken and poultry in general, and the like. Accordingly, the present invention lies in the simultaneous or substantially concurrent administration of an effective dose of glucosamine and cartilage to a patient suffering from an inflammatory disorder, as more fully described below.

In accordance with the invention, cartilage is ground to a fine powder, suitably after being frozen with liquid nitrogen or dry ice. It can then be incorporated in a suitable ointment, cream, or lotion base for topical application, or suspended in physiological saline for injection, in each case with a suitable quantity of glucosamine.

If desired, the powdered cartilage can be extracted with water and the water extract subjected to chromatographic fractionation in a conventional manner (e.g., in a silica or alumina column), whereupon I find that the fraction of greater than 100,000 molecular weight contains most of the anti-inflammatory activity. The fraction thus obtained can be used in the same way as the original powdered cartilage, and has the advantage that it does not contain the collagens that form 40 to 60% of the original cartilage, thereby providing a preparation of greater pharmaceutical elegance, and, if injected, allowing the volume for injection to be reduced. The total cartilage, however, is somewhat more active, and appears therefore to contain minor components of significant effect.

As disclosed in my earlier application, a pro-inflammatory effect is exhibited by the fraction of less than 50,000 molecular weight obtained upon chromatographic fractionation of the water extract of shark cartilage. Accordingly, an improvement in the cartilage itself is obtained by extracting with water, chromatographically fractionating the extract, and separating and adding back the greater than 100,000 molecular weight fraction to the extracted cartilage.

In preparing cartilage for use in the present invention, bones are removed and discarded, and extraneous flesh is cut away. The cartilage is chopped into small pieces, frozen, crushed, and ground to a powder in a pulverizing mill. The powder can be used directly for extraction, but preferably (especially for injection) it should be further ground in a micronizer to a particle size less than 100 microns.

Extraction of the cartilage powder, if desired, can suitably be carried out with water at temperatures from just above freezing to around 50° C. for a period of about 4 to 24 hours or more, preferably between about 20 and about 30° C. for a period of about 6 hours. While the anti-inflammatory acitivty is stable for 20 minutes at 75° C., elevated temperatures should preferably be avoided to prevent loss of activity when relatively long extraction periods are employed. The ratio of water to cartilage can vary over a wide range, as will be apparent to those skilled in this art. For a single-stage extraction, the ratio may suitably be 5 parts of water per part of cartilage by weight to produce an extract of minimum concentration. For maximum recovery of the desired solute, much higher ratios may be used; e.g., 10:1, 25:1, 50:1. Preferably, however, the extraction is carried out countercurrently, with each portion of water successively contacting individual portions of cartilage in sequence, beginning with essentially exhausted cartilage and ending with fresh cartilage. In this way, maximum recovery of solubles is achieved, and the final extract has the maximum content of solubles.

The synergistic combination of my invention is produced by combining glucosamine, suitably as the free base or as the hydrochloride, sulfate, or other salt with a pharmaceutically acceptable acid, with the cartilage powder or extract fashion, or with the materials prepared therefrom for administration. The proportion of glucosamine to cartilage can suitably be between about 5:1 and about 1:5 by weight, although it will be apparent that the synergistic effect will be observed in lesser degree at a wider range. For use with the greater than 100,000 molecular weight extract fraction, the proportion of glucosamine to dissolved matter can suitably be between about 10:1 and about 1:10 by weight. Alternatively, for injection, the glucosamine can be added in the form of a precursor substance such as glutamine, tryptophan, cysteine, or a similar amino acid which is capable of donating an amine group to a hexose such as fructose in the physiological environment to produce glucosamine.

The cartilage, cartilage extract, or the greater than 100,000 molecular weight fraction thereof plus glucosamine, is conveniently sterile-filled into vials, ampoules, or syringes, or is sterile-filled into vials and lyophilized.

The compositions of my invention are effective in a variety of conditions which have an inflammatory component, including rheumatoid arthritis (especially of the small joints, e.g., fingers and wrists), osteoarthritis, acne, psoriasis, hemorrhoids, contact dermatitis, neurodermatitis, and others.

For injection to control rheumatoid arthritis, osteoarthritis, total-body psoriasis, lupus, scleroderma, or other systemic conditions, doses of around 5 to 25 mg of cartilage powder may be given per kilogram of patient body weight, or around 2 to 10 mg/kg of the greater than 100,000 molecular weight extract fraction solids, in each case together with around 5 to 25 mg/kg of glucosamine or an equivalent amount of glucosamine precursor. A suitable carrier liquid is used, preferably isotonic saline.

For topical application, the medication can be added to a suitable ointment, cream, or lotion base in a proportion between about 0.25 and about 5% of solids by weight, for example, around 1%. Typical bases include Dermabase, a standard preparation designed to assist the drug in penetrating the skin, consisting of mineral oil, stearyl alcohol, propylene glycol, synthetic spermaceti, glyceryl stearate, sodium lauryl sulfate, lecithin, methylparaben, and water. Cocoa butter is a suitable base for use with hemorrhoids. For psoriasis, a conventional 5% coal tar ointment is suitable as a base, or Dermabase to which 5% coal tar has been added.

The invention, including the best mode thereof as presently known, is illustrated by the following operating examples.

EXAMPLE 1

Whole shark cartilage was finely chopped, frozen in liquid nitrogen, ground in a blendor, and further ground in liquid nitrogen in a mortar and pestle.

A water extract of the resulting powdered shark cartilage was prepared by suspending one kilogram of the powder in 36 liters of distilled water in a Bellco Glass Microcarrier Spinner Flask and mixing with a magnetic stirrer at 5° C. for 24 hours. The supernatant was syphoned off and fractionated on an Amicon DC-30 High-Yield Fiber Dialyzer/Concentrator. The greater than 100,000 molecular weight fraction was separated and concentrated with a filter allowing substances of less than 2,000 molecular weight to pass through, thereby removing salts. The purified greater than 100,000 molecular weight fraction was lyophilized for future use.

Topical test creams were prepared by suspending the following materials in Dermabase cream (from Marcelle Cosmetics, Plattsburgh, New York), a base selected for its minimal and predictable effects on the topical inflammatory response, using standard pharmaceutical techniques to insure an even distribution of test materials:

1. None (Dermabase cream only)
2. 
   0.5% powdered shark cartilage plus
   0.5% glucosamine hydrochloride
3. 5% powdered shark cartilage
4. 
   0.5% >100,000 mw fraction of powdered shark shark cartilage, plus
   0.5% glucosamine hydrochloride
5. 5% >100,000 mw fraction
6. 5% glucosamine hydrochloride For further comparison, topical test materials were also prepared with lipopolysaccharides and with hydrocortisone:

7. 
   0.5% lipopolysaccharides plus
   0.5% glucosamine hydrochloride
8. 5% lipopolysaccharides
9. 1% hydrocortisone Strain II male and female guinea pigs weighing at least 450 g were divided into groups of five. Approximately five hours prior to each experiment, the animals were shaved on both flanks. At time zero, 10% croton oil in acetone was applied to each side within a 30 mm diameter ring. Fifty to sixty minutes after the application of the croton oil, 0.5 to 0.75 gram of a topical test material was applied to one flank and rubbed into the skin. The opposite flank received the Dermabase alone. All test materials were applied in a randomized, double-blind fashion and, once incorporated into the Dermabase, could not be distinguished. A waiting period of at least 50 minutes insured the absorption of the croton oil and produced an inflammatory reaction that a 1% hydrocortisone cream did not completely inhibit. A second treatment with the test material was applied approximately 45 minutes after the first treatment. The reactions reached a maximum by the end of 24 hours, at which time the flanks were measured for erythema and induration. Double skin (i.e., pinched skin) thickness readings were taken with a Schnelltäster caliper. Each of these two criteria were assigned standard scores as follows:

| Score | Erythema | Double Skin Thickness (mm × 10) |
|---|---|---|
| 0 | trace | <3 |
| 1 | light pink | ≧3 | <6 |
| 2 | pink | ≧6 | <10 |
| 3 | dark pink | ≧10 | <15 |
| 4 | +1E* | ≧15 | <20 |
| 5 | +2E* | ≧20 | <25 |
| 6 | +3E* | ≧25 | <30 |
| 7 | >+3E* | ≧30 |

*Degrees of redness as defined by Blazkovek et al, "A Study of Passive Cellular Transfer of Local Cutaneous Hypersensitivity," Int. Arch. Allergy, 27, 289-303 (1965).

The results of the tests were as follows:

| Treatment No. | Treating Agent | Mean Skin Reactivity ±Standard Error | |
|---|---|---|---|
| | | Treatment | Control |
| 1. | None | 9.2 ± 0.7 | 8.6 ± 0.7 |
| 2. | 0.5% cartilage powder 0.5% glucosamine HCl | 1.4 ± 0.7 | 10.8 ± 0.6 |
| 3. | 5% cartilage powder | 2.8 ± 0.6 | 9.8 ± 0.6 |
| 4. | 0.5% > 100,000 mw fraction 0.5% glucosamine HCl | 2.2 ± 1.0 | 7.4 ± 1.4 |
| 5. | 5% > 100,000 mw fraction | 6.0 ± 0.8 | 9.2 ± 1.5 |
| 6. | 5% glucosamine HCl | 7.0 ± 0.8 | 9.8 ± 0.5 |
| 7. | 0.5% lipopolysaccharides | 7.0 ± 0.8 | 6.2 ± 0.8 |

| Treatment No. | Treating Agent | Mean Skin Reactivity ±Standard Error | |
|---|---|---|---|
| | | Treatment | Control |
| 8. | 0.5% glucosamine HCl 5% lipopolysaccharides | 10.0 ± 0.4 | 9.3 ± 0.8 |
| 9. | 1% hydrocortisone | 3.5 ± 0.5 | 8.3 ± 0.3 |

EXAMPLE 2

Whole bovine cartilage from the trachea was firmly chopped, frozen in liquid nitrogen, ground in a blender, and further ground to a powder in liquid nitrogen in a mortar and pestle. The powder was incorporated into Dermabase cream in three preparations, 5% by weight alone, 2% by weight alone, and 0.5% by weight plus 0.5% by weight glucosamine. The preparations were tested as in Example 1, with the following results:

| Treatment Agent | Mean Skin Reactivity ±Standard Error | |
|---|---|---|
| | Treatment | Control |
| 5% cartilage powder | 0.9 ± 0.04 | 3.0 ± 0.66 |
| 2% cartilage powder | 2.25 ± 0.69 | 2.0 ± 0.81 |
| 0.5% cartilage powder 0.5% glucosamine | 0.5 ± 0.66 | 1.2 ± 0.56 |

The data demonstrate that bovine cartilage, when used alone at 5% concentration, has anti-inflammatory activity, as has been previously reported; but when used at a concentration of 0.5% in combination with 0.5% glucosamine, the observed anti-inflammatory effect is greater than that produced by either ingredient along (compare the test result in Example 1 on glucosamine alone).

EXAMPLE 3

Chicken cartilage was preparted and tested according to the procedure described in Example 2, with the following results:

| Treating Agent | Mean Skin Reactivity ±Standard Error | |
|---|---|---|
| | Treatment | Control |
| 5% cartilage powder | 2.2 ± 1.40 | 3.3 ± 1.13 |
| 2% cartilage powder | 3.6 ± 0.14 | 3.2 ± 0.14 |
| 0.5% cartilage powder 0.5% glucosamine | 0.7 ± 0.4 | 3.0 ± 0.52 |

The data demonstrate that chicken cartilage, like shark cartilage and bovine cartilage, acts synergistically with glucosamine in producing an anti-inflammatory effect.

While I have described my invention with reference to certain specific examples thereof, it is to be understood that such matters are offered as illustrations only and not by way of limitation. Numerous modifications and equivalents of the invention will be apparent to those skilled in the art from the present description and claims.

What is claimed is:

1. A method for the treatment disorders having an inflammatory component which comprises administering to the patient a synergistic therapeutic dose of cartilage and glucosamine.

2. The method of claim 1 wherein said cartilage is administered in the form of whole cartilage powder.

3. The method of claim 1 wherein said cartilage is administered in the form of the greater than 100,000 molecular weight fraction of an aqueous extract of whole cartilage.

4. The method of claim 1 wherein said cartilage and glucosamine are applied topically.

5. The method of claim 1 wherein said cartilage and glucosamine are administered parenterally.

6. The method of claim 1 wherein said cartilage is bovine cartilage.

7. The method of claim 1 wherein said cartilage is chicken cartilage.

8. The method of claim 1 wherein said glucosamine is administered in the form of a substance affording glucosamine under the conditions of treatment.

9. The method of claim 1 wherein said cartilage and said glucosamine are administered in a weight proportion between about 5:1 and about 1:5.

10. A method for the treatment of disorders having an inflammatory component which comprises administering to the patient a synergistic therapeutic dose of shark cartilage and glucosamine.

11. The method of claim 10 wherein said cartilage is administered in the form of whole shark cartilage powder.

12. The method of claim 10 wherein said cartilage is administered in the form of the greater than 100,000 molecular weight fraction of an aqueous extract of whole shark cartilage.

13. The method of claim 10 wherein said cartilage and glucosamine are applied topically.

14. The method of claim 10 wherein said cartilage and glucosamine are administered parenterally.

15. The method of claim 10 wherein said glucosamine is administered in the form of a substance affording glucosamine under the conditions of treatment.

16. An anti-inflammatory composition comprising essentially whole cartilage and glucosamine in a synergistic weight proportion between about 5:1 and about 1:5.

17. The anti-inflammatory composition of claim 16 wherein said cartilage is shark cartilage.

18. A composition as in claim 16 comprising essentially glucosamine and the greater than 100,000 molecular weight fraction of an aqueous extract of whole cartilage.

19. The anti-inflammatory composition of claim 18 wherein said cartilage is shark cartilage.

20. A composition as in claim 16 comprising whole cartilage and a substance affording glucosamine under the conditions of use of the said composition for treating disorders having an inflammatory component.

21. The anti-inflammatory composition of claim 20 wherein said cartilage is shark cartilage.

* * * * *

UNITED STATES PATENT AND TRADEMARK OFFICE
CERTIFICATE OF CORRECTION

PATENT NO.   :   4,473,551
DATED        :   September 25, 1984
INVENTOR(S)  :   Michael Schinitsky It is certified that error appears in the above-identified patent and that said Letters Patent is hereby corrected as shown below:

Column 2, line 40, "acitivty" should be --activity--.

Column 2, line 47 and line 48, "minimum" should be --maximum--.

Column 2, line 61, "fashion" should be --fraction--.

Signed and Sealed this

Twelfth Day of March 1985

[SEAL]

Attest:

DONALD J. QUIGG

Attesting Officer   Acting Commissioner of Patents and Trademarks